US012599505B2

(12) United States Patent　　　　　(10) Patent No.: US 12,599,505 B2
Lipshaw et al.　　　　　　　　　　　(45) Date of Patent: Apr. 14, 2026

(54) COMPRESSION GARMENT AND METHOD FOR MANUFACTURING A COMPRESSION GARMENT

(71) Applicant: MEDI USA, L.P., Whitsett, NC (US)

(72) Inventors: Moses Lipshaw, Hillsborough, NC (US); Jody Erickson, Hillsborough, NC (US); Thomas Wright, Raleigh, NC (US); Glenn Anderson, Elon, NC (US)

(73) Assignee: Medi USA, L.P., Whitsett, NC (US)

( * ) Notice: Subject to any disclaimer, the term of this patent is extended or adjusted under 35 U.S.C. 154(b) by 766 days.

(21) Appl. No.: 17/838,944

(22) Filed: Jun. 13, 2022

(65) Prior Publication Data

US 2022/0395403 A1　　Dec. 15, 2022

(30) Foreign Application Priority Data

Jun. 14, 2021　(EP) ...................................... 21179354

(51) Int. Cl.
*A61F 13/10*　　　(2006.01)
*A61H 7/00*　　　(2006.01)

(52) U.S. Cl.
CPC .............. *A61F 13/10* (2013.01); *A61H 7/001* (2013.01); *A61H 2201/1635* (2013.01); *A61H 2201/165* (2013.01); *A61H 2201/1695* (2013.01)

(58) Field of Classification Search
CPC .......... A61F 13/10; A61F 13/08; A61F 13/06; A61F 13/061; A61F 13/064; A61F 13/101; A61F 13/104; A61F 13/107; A61F 15/004; A61H 7/001; A61H 2201/1635; A61H 2201/165; A61H 2201/1695; A41D 19/0006; A41D 19/001
See application file for complete search history.

(56) References Cited

U.S. PATENT DOCUMENTS

| | | | | |
|---|---|---|---|---|
| 3,459,179 | A | * | 8/1969 | Olesen ................... A47C 27/12 |
| | | | | 5/655.4 |
| 4,657,003 | A | * | 4/1987 | Wirtz .................. A61F 5/05833 |
| | | | | 128/869 |
| 5,152,019 | A | | 10/1992 | Hirata |
| 5,618,263 | A | * | 4/1997 | Alivizatos ........... A61F 5/05841 |
| | | | | 128/882 |
| 5,940,888 | A | * | 8/1999 | Sher ......................... A41C 3/12 |
| | | | | 450/38 |
| 6,453,477 | B1 | | 9/2002 | Bainbridge |
| 6,656,141 | B1 | * | 12/2003 | Reid .................. A61B 17/1325 |
| | | | | 601/134 |

(Continued)

FOREIGN PATENT DOCUMENTS

| | | |
|---|---|---|
| BR | 102014018098 | 2/2015 |
| DE | 3806456 | 11/1989 |

(Continued)

*Primary Examiner* — Andrew Restaino

(74) *Attorney, Agent, or Firm* — Rimon PC

(57) ABSTRACT

The invention concerns a compression garment for providing compression to a body part, in particular a limb, of a patient, comprising an, in particular tubular, padded sleeve extending around the body part and having an inner layer and an outer layer secured, in particular sewn, together to define at least one enclosure between them, and multiple particles, in particular plastic foam particles, received in the enclosure for being pressed against the body part.

18 Claims, 8 Drawing Sheets

(56) References Cited

U.S. PATENT DOCUMENTS

| | | | | |
|---|---|---|---|---|
| 6,891,078 | B1 | 5/2005 | Dillard | |
| 7,662,468 | B2 | 2/2010 | Bainbridge | |
| 7,767,874 | B2 | 8/2010 | Kellogg | |
| 10,863,836 | B2 | 12/2020 | Randall | |
| 2003/0045821 | A1 | 3/2003 | Iker | |
| 2004/0210176 | A1* | 10/2004 | Diana | A61H 23/04 |
| | | | | 601/151 |
| 2005/0261617 | A1* | 11/2005 | Hall | A61F 13/08 |
| | | | | 602/62 |
| 2007/0276310 | A1 | 11/2007 | Lipshaw et al. | |
| 2008/0086071 | A1 | 4/2008 | Weatherly | |
| 2008/0125688 | A1* | 5/2008 | Kellogg | A61F 13/10 |
| | | | | 602/61 |
| 2008/0189829 | A1* | 8/2008 | Fusco | A61F 13/08 |
| | | | | 2/239 |
| 2010/0031260 | A1* | 2/2010 | Morocz | G06F 9/485 |
| | | | | 718/100 |

| | | | |
|---|---|---|---|
| 2012/0095419 | A1 | 4/2012 | Riesinger |
| 2021/0177071 | A1 | 6/2021 | Hernandez |

FOREIGN PATENT DOCUMENTS

| | | | |
|---|---|---|---|
| DE | 202018100712 | | 4/2018 |
| EP | 812154 | | 12/1997 |
| EP | 1025767 | | 8/2000 |
| EP | 1926458 | | 6/2008 |
| EP | 2323603 | | 5/2011 |
| EP | 3128968 | | 2/2017 |
| EP | 3288511 | | 3/2018 |
| FR | 2635650 | | 3/1990 |
| JP | H0121939 | * | 10/1985 |
| WO | 9930607 | A2 | 6/1999 |
| WO | 2010073921 | | 7/2010 |
| WO | 2015153343 | | 10/2015 |
| WO | 2019020155 | | 1/2019 |
| WO | 2022103850 | | 5/2022 |

* cited by examiner

30

26

1

1

30

14

26

15a

15b

26

15c

COMPRESSION GARMENT AND METHOD FOR MANUFACTURING A COMPRESSION GARMENT

CROSS REFERENCE TO RELATED APPLICATIONS

This application claims benefit to European application number 21179354.2, filed on Jun. 14, 2021. The above referenced patent application is incorporated by reference in its entirety.

BACKGROUND OF THE INVENTION

Edema is a medical condition of a person, in particular a patient, in which a body fluid excessively accumulates in a body part, for example arms, legs or trunk, instead of being naturally transported in the respective anatomical system. Edema can have a variety of causes, for example radiation therapy, injuries, infections, and other circumstances which result in damage to or destruction of portions of the anatomical system, in particular the lymphatic or venous system. Edema often causes swelling of the body part and may have further symptoms.

An important case is lymphedema, that is, the accumulation of excessive lymph fluid in a body part. Lymphedema often occurs when breast cancer is treated, in particular in at least one arm of the patient, and causes painful swelling.

Many treatments have already been proposed in the art which usually apply decongestive therapy, wherein the unwanted fluid is drained from the body part, for example staged pumps sequentially compressing different areas of the body part such that uniform annular pressure, that is, pressure completely circumscribing the body part, is applied. In this manner, the accumulated fluid is transported to healthy pathways, for example to a working part of the lymphatic system. However, apart from these active systems, for the use of which the patient is effectively immobilized, passive systems, in particular compression garments, have also been proposed in the art.

In U.S. Pat. No. 5,916,183 A, an apparatus for treating lymphedema is proposed, having a sleeve with inwardly projecting-elastomeric fingers and externally fitted pressure adjusting circular bands. When the sleeve is fitted to a patient's limb, the fingers impose a grid pattern of pressure points against the skin of swollen limb. Space around and between the pressure points provides channels under the skin, through which lymphatic fluids are able to migrate up the arm to the shoulder, where healthy nodes process it and channel it to the large veins. This is also applicable to other limbs, hands, and feet with sleeves, and to the shoulder, chest wall, and back with vests. The fingers are, in particular, provided by a sheet of convoluted plastic foam which, when unrolled, has a plurality of protuberances projecting upwardly from a base surface thereof. This apparatus is improved according to U.S. Pat. No. 7,584,755 B2 by additionally using a second sleeve received over the first sleeve having the fingers to increase the therapeutic pressure applied to the limb.

U.S. Pat. No. 5,976,099 A discloses a method and apparatus for the alleviation of an undesirable fluid accumulation in a body area of a patient. The apparatus, or static reaction system, has an enclosure containing a multiplicity of particles that are pressed against the body area. The shape of the enclosure and the physical qualities of the particles affect the suitability of specific versions of the method and apparatus to particular conditions and body areas. Pockets are included in some versions of the enclosure to capture and isolate subsets of the multiplicity of particles. An optional directional flow pattern feature is established by the orientation, sizes and shapes of the optional pockets and thereby affects the rate at which the fluid accumulation is reduced. The enclosure is optionally constructed with low friction, porous and breathing fabrics and materials to improve patient comfort and patient compliance. The enclosure is pressed, held and/or forced against a selected body area by means of a detachable compression cover, a pneumatic pack, compressive bandaging or wrapping, and made with velcro stretch fabric and/or with velcro strapping or other suitable means.

In U.S. Pat. No. 7,135,007 A, a compression garment for compressing a portion of a body of a patient includes a tubular body. The body includes an outer layer and an inner layer secured to the outer layer. The inner layer at least partially bounds a channel adapted to receive a portion of a body of a patient. The inner layer includes a backing having a plurality of pressure projections extending therefrom, which may be patches or ribs in any desired form or size. A layer of compressible cushioning material is disposed between the outer layer and the inner layer. Compression straps are disposed on the body for selectively constricting the body.

U.S. Pat. No. 7,767,874 A describes a patient-friendly medical device for removal of excess fluids from body tissue. The device is particularly useful to treat soft tissue inflammation, damage, edema and/or lymphedema. It comprises a composite multilayered assembly that provides a gradient pressure compression device to compress body tissue of a patient in a controlled and graduated manner. The composite multilayered assembly can have an inner and/or outer layer to enhance uniform distribution of compression about the affected portion of the patient and can have flexible intermediate layers with elastomeric components such as foamed chips, foamed pieces, and/or chopped foam that can have a different density and/or size and/or shape to form channels (canals) therebetween to enhance flow of excess fluids from the body tissue of the patient. The channels or canals can create zones of gradient pressure to help move excess fluid from the tissue of the affected portion of the body of the patient.

However, there is still room for improvement of known compression garments using a padded sleeve, in particular a padded foam sleeve. Padded foam sleeves are known to trap moisture and heat resulting in user discomfort. If foam particles are used, repeated stretching and compressing deteriorates and compacts these fine irregularly shaped foam particles. If, on the other hand, continuous sheet foam and/or particle/sheet bonded composites are used, air flow is prevented and the sheets tend to tear from repeated stress. Furthermore, these designs also provide for only one topography surface type to engage the body part.

It is an object of the current invention to provide an improved compression garment for treating edema in a patient, in particular providing better comfort for the user, improved treatment even after multiple uses and flexibility regarding treatment modes.

This object is achieved by providing a compression garment and a method for manufacturing a compression garment according to the independent claims. Advantageous embodiments are described in the dependent claims.

SUMMARY

In a compression garment for providing compression to a body part, in particular a limb, of a patient, in particular for treating edema, the compression garment comprises an, in particular tubular, padded sleeve extending around the body part having an inner layer and an outer layer secured, in particular sewn, together to define at least one enclosure between them, and multiple particles, in particular plastic foam particles, received in the enclosure for being pressed against the body part, Wherein, according to the invention, the particles have an at least essentially polyhedral shape such that an irregular pattern of flat surfaces and edged protrusions is formed at least on the inner layer side of the enclosure.

DETAILED DESCRIPTION OF THE EMBODIMENTS

Hence, a padded sleeve enclosing the body part is used as a body. In particular, the inner layer contacts the skin, providing locally varying pressure due to the irregular pattern provided by the particles. In other words, the irregular pattern defines a certain particle topography on the inner layer side of the enclosure, which is transformed into a randomized, that is also irregular, contact surface topography of the inner layer to the patient, wherein the irregular contact surface topography comprises flat surface portions and contoured surface protrusions to distribute compression to the body part.

The particles are, preferably, foam particles, in particular plastic foam particles. Materials already used in the art for padding applications in compression garments may also be employed here. For example, the particles may be made from polyurethane foam, preferably having a density between 2 and 3.5 pounds per cubic foot, more preferably between 2.5 and 2.9 pounds per cubic foot, and an impression load deflection (ILD) firmness of 50 to 80, preferably 60 to 70. Higher density foams are known to be more durable than lower density equivalents, and a higher initial firmness (ILD) retains a greater average level of firmness over the material life cycle than lower firmness equivalents. Preferably, the particles may be water jet or die cut from sheet foam.

According to the invention, polyhedral, preferably cubic, particles are used as a foam layer between the inner and outer layers. The particles are placed randomly in the enclosure, resulting in the irregular pattern. Polyhedrons are three dimensional shapes with flat polygonal faces and sharp edges. In the compression garment, the particles are at least essentially polyhedral, since, for example due to their production, the sharpness of edges and/or corners may vary, such that, for example, slightly rounded corners and/or edges may occur. Such productional variations are understood to be within tolerances, such that the particles may still be understood as polyhedral. Preferably, cubic particles are used, however, the particles may also be tetrahedrons or cuboctahedrons, wherein the number of faces is generally preferably equal or smaller than eight. The particles are preferably uniform in size and shape, that is, have at least essentially the same dimensions and/or shape. For example, all particles may, preferably, be cubes.

Furthermore, the particles are advantageously chosen to be larger than particles used in the state of the art. For example, the edges of the particles may have a length of at least 0.75 cm, in particular at least 1 cm. In particular, the dimensions of the particles, for example their edge lengths, may be from 0.75 to 1.75 cm. In an especially preferred example, the particles may be cubes having a size of approximately 0.5 inch×0.5 inch×0.5 inch.

When placed inside the enclosure, the polyhedral, in particular cubed, geometry provides for randomized flat surface and contoured surface protrusions to distribute compression to the body. Further, the relatively large size and geometry of the particles, compared to finer chipped and shredded alternatives in the state of the art, provides for reduced particle surface areas and increased air space between particles with less compacting. The reduced surface area and defined polyhedral geometry improves the, in particular foam, particles' structural durability and retention of firmness over time, whereas irregular particles, as used before, tend to break down, deteriorate into smaller particulates and compact over time. Hence, uniform polyhedral particles not only provide both non-aggressive flat surfaces and peak protrusions to promote edema fluid flow, but also increase foam longevity. The increased air space between larger, polyhedral geometry non-compacted particles further promotes air, heat and moisture transfer compared to finer compacted particles and continuous foam sheet alternatives.

That is, preferably, the particles arranged in the enclosure form air passages from the inner layer to the outer layer. Because of the edged, clearly defined polyhedrons, in particular cubes, arranged irregularly in the enclosure, free spaces between particles are formed which may function as cooling passages, guiding heat and/or moisture away from the body part, such that the comfort is increased, in particular compared to smaller, irregularly formed and/or shredded particles or foam sheets, which block the transport of heat and moisture.

In this context, it is particularly preferred that the inner layer and the outer layer are made of an, in particular moisture-wicking and/or temperature regulating, fabric. While, in general, any type of material usually used for compression garments may be used as the outer and inner layer, like, for example, cotton, lycra, spandex, other, in particular elastic, fabrics, or combinations thereof, preferably, the used fabric is moisture-wicking and/or temperature regulating. In other words, the proposed large, polyhedral particles leaving free spaces for passages may be combined with cooling fabric inner and outer layers to promote air flow and heat transfer through the whole padded sleeve. The inner and outer fabric layers are engineered to draw heat and moisture away instantly and continuously from the body part, which is facilitated by the cooling passages in the particle layer. A preferred, concrete cooling material, in particular nylon and polyester fibres, for the inner and outer layer is known by the trademark "brrr°" and is available from Brrr!, Inc., Atlanta, Georgia, U.S.A.

In preferred embodiments, the padded sleeve comprises at least one structuring seam structuring the padded sleeve, in particular at least one quilt seam. In many cases, it is advantageous to provide the padded sleeve with a certain structure, in particular channels, promoting the therapeutical use of the compression garment, by, for example, activating certain regions and/or providing flow channels for edema fluid to be removed from the body part. While it is possible that the stitches of such structuring seams only extend through the inner and outer layer, preferably, at least one structural seam is a quilt seam including the layer of particles, in particular by being quilted after introduction of the particles into the enclosure. In other words, preferably at least one stitch of the at least one quilt seam extends through at least one of the particles and/or particles are compressed at the quilt seam such that the padded sleeve is of less thickness.

Structuring seams may thus extend through the composite of the inner and outer layers and the particle layer, preferably by being quilted through the composite (i.e. through the outer layer, through portions of the particles thereby compressing portions of the particles, and through the inner layer), creating channels in the padded sleeve. Secured particles advantageously pad the seam channel areas and form part of the sub-enclosures that trap the remaining free particles. The composite padded sleeve may then comprise of alternating composite layers that switch between a thicker "inner layer-free particles-outer layer" composite layer and a thinner "inner layer-fixed particles-outer layer" composite layer. In preferred embodiments, a thicker "inner cooling fabric-free foam particle-outer cooling fabric" composite layer transitions at a quilt seam to a thinner "fixed cooling fabric-fixed compressed foam particle-fixed outer cooling fabric" composite layer. When the sleeve is formed as a tubular structure from a thus-manufactured panel, these composite layers will, for example, alternate in the distal, proximal, medial, and lateral orientations on the limb, dependent on the quilt seam channel direction.

Generally speaking, in a preferred embodiment, the multiple structuring seams define a pattern of channels extending over the area of the padded sleeve, in particular to facilitate flow to lymphatic pathways. Hence, the result of structuring by the structuring seams can be a pattern of channels facilitating flow of edema fluid, in particular lymph fluid, out of the body part. In particular, the pattern of channels is or comprises a chevron pattern, in particular along a length of a limb as the body part, and/or comprises multiple sub-patterns whose channels at least partly connect to each other, wherein, in particular, an, in proximal-distal direction, central chevron pattern transitions to a straight and/or fanned pattern at the distal and/or proximal ends. Hence, preferably, variable channeling designs from straight to chevron angle to straight to promote edema flow into and out of the zone of compression are conceivable, further complementing the irregular pattern effect of the particles.

For example, in a compression garment for the arm and hand of a patient, in particular suffering from lymphedema, may comprise a straight sub-pattern of channels starting at the fingers, transitioning to chevron channeling through the end of the sleeve. In another example, a straight sub-pattern of channels may extend over the hand, transitioning to a chevron sub-pattern over the arm, and then transitioning back to a straight sub-pattern of channels to exit the sleeve. Hence, generally, the structuring seams may define channels including chevron patterns to facilitate flow to lymphatic pathways and transitions to straight, fanned, or other direct pattern channels at the distal and/or proximal end of the padded sleeve to channel flow into and out of the padded sleeve.

In embodiments, the padded sleeve may be elastic and/or configured to apply compression, in particular in a range of 10 to 20 mmHg, according to a predetermined basic compression profile to the body part. In such embodiments, the padded sleeve itself applies compression to the body part, such that the compression garment may only consist of the padded sleeve itself. A compression in the range of 10 to 20 mmHg, for many standards, corresponds to low or medium compression often used when treating edema. Generally preferably, also with further sleeves as discussed below, the overall compression garment, when worn, is preferably configured to apply graduated compression, in particular for setting a preferred flow direction of the edema fluid out of the treated region of the body part. Such a graduated compression profile may, for example, comprise at least one pressure gradient and comply to a standard, as further discussed below.

In especially advantageous embodiments, the compression garment further comprises at least one oversleeve, which is adapted to be worn over the padded sleeve, and/or at least one undersleeve, which is adapted to be worn under the padded sleeve, wherein the oversleeve and/or the undersleeve comprise at least one, in particular moisture-wicking and/or temperature regulating, fabric layer and are configured to apply compression according to a predetermined additional compression profile to the body part. This, in particular, allows that, by choosing a suitable combination of sleeves, in particular oversleeve, padded sleeve, and/or undersleeve, an effective compression profile may be chosen. In preferred embodiments, the sleeves may be labeled to instruct the user how much standalone and/or additive compression will be applied when the sleeves are separate or combined. This can, in particular when multiple oversleeves and/or undersleeves or even padded sleeves are provided, also be understood as a compression garment system, comprising the building pieces for the compression garment arrangement actually to be worn. Regarding the material of the oversleeve and/or the undersleeve, preferably, the same or a comparable material may be used. In particular, as discussed above, a material that draws heat and moisture away from the body part may be used to further improve wearing comfort. For example, the materials available as "brrr°" may also be used here.

As already indicated, multiple oversleeves and/or undersleeves for selectively applying to the patient may be provided, for example each having different dimensions and/or compression characteristics. In this manner, a configurable compression garment system is provided, opening up a wide range of flexibility and applications, as further discussed below.

The at least one oversleeve and/or undersleeve may have an additional compression profile, in particular to add to the basic compression profile of the padded sleeve and/or another additional compression profile. For example, of the padded sleeve applies compression of about 10 to 20 mmHg, the compression applied by at least one of the at least one oversleeve and/or undersleeve may be in the range of 0 to 10 mmHg and/or of 5 to 15 mmHg, such that, for example, mild compression may be reinforced to medium compression.

In especially preferred embodiments, hence, the basic compression profile and the at least one additional compression profile may be chosen such that they combine to an effective compression profile according to at least one compression class according to at least one guideline or standard. For example, the compression garment according to such an embodiment may comprise an elastic padded sleeve and at least one elastic oversleeve and/or at least one elastic undersleeve. In an example, the compression garment may be applicable to the arm of the patient. The padded sleeve may then be configured to provide 10 to 20 mmHg (15 mmHg nominal) of compression to the arm at the C1 landmark and residual gradient compression levels aligned with the RAL-GZ 387/2 compression standard as a basic compression profile. A "standard" oversleeve or undersleeve may then be configured to provide 0 to 10 mmHg (5 mmHg nominal at C1) and residual gradient compression levels as an additional compression profile such that, when combined with the padded sleeve, the compression garment provides a nominal compression of 20 mmHg (15 mmHg plus 5 mmHg) and an aggregated residual compression profile with continued alignment to RAL mild Class I compression. An optional second, "firm" oversleeve may be configured to provide 5 to 15 mmHg (10 mmHg nominal) and be alternatively combined with the padded sleeve resulting in a worn combination that provides a nominal compression of 25 mmHg (15 mmHg plus 10 mmHg) and an aggregated residual compression profile aligned with RAL moderate Class II compression. These mild and moderate compression classes are the most utilized for management of edema while at rest and supine, when the gravitational effects on pooling edema fluid are reduced. Compression garments according to the invention, which may, of course, generally be made to measure, are further configurable to other graduated compression profiles, such that single sleeves and/or combinations of sleeves conform to other RAL classifications and/or compression classifications of other standards or guidelines. It should be noted that the padded sleeve can be configured for use as a standalone compression device to implement a certain compression profile (namely as the basic compression profile), so that compression may also be applied without the need for an oversleeve or undersleeve. In another embodiment, the padded sleeve can be configured to provide little to no compression for use as sub-surface beneath an oversleeve as discussed above or other compression devices acting as oversleeves, e.g., bandaging, inelastic wraps, etc., to distribute compression. That is, the compression garment may also comprise a bandage and/or an, in particular inelastic wrap, which may be used as "adjustable" oversleeve.

In summary, by a compression garment having a padded sleeve and at least one undersleeve and/or at least one oversleeve, a compression garment system with configurable compression and a residual graduated compression profile can be provided, in particular allowing the ability to change between compression classes. The configuration principles described can be applied to other compression classification systems and for different areas of the body such as the upper extremities, the lower extremities, the head, the neck, the torso and the trunk.

In preferred embodiments, at least one of the at least one oversleeve may be shorter in proximal-distal-direction than the padded sleeve and/or at least one of the at least one undersleeve may comprise an outer low friction surface. When an oversleeve is applied over the padded sleeve, its dimensions are preferably shorter than the padded sleeve. This allows the binding finished edges of the oversleeve to rest on the padded sleeve, which aids in preventing sensitivities and irritation to the oversleeve edges. Regarding undersleeves, preferably, an outer low friction surface may serve as a donning aid for the padded sleeve. For example, the at least one undersleeve may be a compressive liner, in particular made of a smooth material. In such an embodiment, the low friction surface helps the irregular inner surface of the padded sleeve to more easily slide over the body part, in particular limb.

Further preferably, multiple oversleeves and/or undersleeves of different dimensions or shapes for selectively applying to the patient may be provided for covering different portions of the body part and/or the padded sleeve. For example, it can be provided that the undersleeve comprises an arm portion and a hand portion, in particular also a finger portion, wherein the padded sleeve extends over the arm portion of the undersleeve, such that, in particular a hybrid glove/hand sleeve/arm sleeve may be realized. But also generally, unique compression undersleeve, padded sleeve, and/or oversleeve pairings can be created to achieve a desired overall compression profile and preferred coverage of each sleeve regarding the body part. In the concrete example, an undersleeve with finger, hand, and arm coverage could be configured to provide stronger compression to the hand and finger area, where the thicker padded sleeve coverage may not be desirable. The padded sleeve would then be configured to start compressing where the stronger compression in the hand undersleeve ends.

In this context, preferably, at least one of the at least one undersleeve and/or the padded sleeve may comprise indicia for positioning the padded sleeve on the undersleeve and/or at least one of the at least one oversleeve on the padded sleeve and/or the undersleeve. These indicia may form a marking system, preferably on the on the undersleeve and/or the padded sleeve. Such a system could guide the user to proper alignment of the sleeve compression zones to achieve the desired cumulative effect. As already discussed above, the undersleeve and/or padded sleeve and/or oversleeve compression zones can be further labeled to instruct the user how much standalone and additive compression will be applied when the sleeves are separate or combined, in particular by providing compression indicia of a labeling system.

In preferred embodiments, the oversleeve and the padded sleeve may comprise corresponding fastening means for detachably fastening the oversleeve to the padded sleeve in at least one position. Such fastening means may, for example, comprise hook-and-loop fasteners, snap fasteners, and/or button fasteners. In embodiments, a button loop attachment may be added to interface with a button of the padded sleeve to anchor the oversleeve in place.

In an especially preferred embodiment, however, the fastening means of the padded sleeve comprise at least one donning band having fixed ends secured to the outer layer and free ends detachably fastened to each other by a fastener, wherein the fastening means of the oversleeve comprise two perforations for the donning band, such that, in particular, the donning band can still be used to aid in donning or undonning the compression garment as a whole, that is, also comprising the oversleeve. The fastener may, for example, comprise a button-and-loop fastener and/or a snap fastener and/or a hook-and-loop fastener. The fixed ends may, for example, be sewn to the outer layer. A donning aid like the donning band comfortably allows donning the padded sleeve, despite the irregular contact surface topography caused by the arrangement and type of the particles on the inner side of the enclosure.

The padded sleeve and oversleeve can thus be configured to allow a donning band (which may also be called donning loop, donning strap, loop handle, or handle strap) to pass, in particular with a handle portion, through the oversleeve. This provides an interface to anchor the oversleeve in place and allows the user to don both sleeves simultaneously while using the handle portion of the at least one donning band, in particular increasing comfort with regard to the irregular contact surface topography of the inner layer. To this end, perforations may be created in the oversleeve to allow the donning band to pass through the oversleeve The perforations may be slightly larger than the donning band material or, alternatively, be smaller than the donning band material, but be elastic and expand to allow the donning band to pass through. Preferably, multiple donning bands are provided at different positions on the padded sleeve. Hence, multiple anchoring areas for the oversleeve may be provided. The donning bands may be configured to have fixed ends sewn to the padded sleeve and free ends that are releasably attached to each other via hook and loop, buttons, snaps, or other means. Once the free ends are threaded through the oversleeve perforations, they may be reconnected using the fastener to again provide an operational handle.

It is noted that such donning bands are also generally advantageous in the inventive garment. In particular, the padded sleeve may comprise at least one donning band on the outer layer, in particular one or two in a proximal end area and one or two in a distal end area. Donning bands may this be, for example, sewn to the distal and proximal areas of the padded sleeve to help the user don the padded sleeve, in particular despite the irregular surface of the inner layer due to the irregular pattern of the particles. In particular, they may be sewn to the outer layer. In principle, oversleeves and/or undersleeves may also comprise donning aids, however, preferably regarding the oversleeve, donning bands on the padded sleeve may be used for both the padded sleeve and the oversleeve, as described above.

The compression garment may have a shape corresponding to the body part, in particular the limb. For example, the body part may be an upper extremity, for example an arm including or not including a hand, a tentacle, or the hand; a lower extremity, for example a leg including or not including a foot, or the foot; a neck, a torso, a trunk and/or a head. Preferably, the compression garment may be designed for an upper extremity. For example, the padded sleeve may be configured to cover the hand, arm, and/or shoulder, wherein in the latter case an oblique proximal rise may be provided. Coverage can be further configured to include a thumb post/thumb hole, or partial hand/arm coverage. Of course, the compression garment may also be made to measure for certain patients.

In particularly preferred embodiments, the compression garment may be configured to be applied to the fingers of a hand, wherein finger channels for receiving the fingers are provided by quilting opposing parts of the whole padded sleeve, that is, through two sets of inner layer, outer layer, and particles in the enclosure. Similar approaches may be applied for the lower extremities and/or other body parts.

The oversleeve and/or undersleeve, if provided, may be constructed like the padded sleeve, but, in particular, with only single material layer panel(s). In particular, the oversleeve and/or the undersleeve may comprise layers made of the same material or materials as the inner and outer layer of the padded sleeve, as described above, and/or may be elastic.

In preferred embodiments, that the padded sleeve may comprise multiple different structure areas along the proximal-distal-direction, wherein at least one structure area comprises the particles in the enclosure resulting in an irregular contact surface topography of the inner layer towards the patient, while at least one other structure area comprises a different, second contact surface topography. In this manner, the compression garment, in particular its padded sleeve, can be further configured to meet the needs of a patient by providing different forms of pressure and pressure patterns to different portions/areas of the body part. To this end, the topographies actually acting on the body part differ along its length, such that, in particular, each structure area may be associated to at least one body part area. The second contact surface topographies may be implemented in a variety of ways, however, in preferred embodiments, additional enclosures may be provided and filled with additional topography conferring layers.

In preferred embodiments, a flat or regularly structured foam layer may arranged between the inner and the outer layer to provide the second contact surface topography. For example, a padded sleeve for the arm and hand could have a hand region, where a flat foam layer is used between the outer and inner layers, that then transitions into free polyhedral particles in the enclosure in the arm area.

In a further, especially advantageous embodiment, the padded sleeve further comprises at least one foam layer between the particles and the outer layer in the enclosure, the foam layer having an outer layer side topography differing from the inner layer side topography provided by the particles, in particular a flat or regularly structured outer layer side topography, such that the padded sleeve can be reversed to apply the outer layer side topography to the body part. This allows flexible use of the compression garment for different medical conditions and/or different stages of treatment. For example, a layer structure of outer layer-foam layer-particles-inner layer may be used in both the original and the reverse orientation. Since the particles are relatively large, as discussed above, in embodiments, in particular depending on the outer layer side topography to be conferred, the foam layer may comprise at least one through opening to continue cooling passages provided by the particles, wherein the through opening may have dimensions smaller than the dimensions of the particles.

It is noted that, since the inner and outer layer are preferably identical in material and configuration, already a padded sleeve having only the inner layer, the outer layer and the particles therebetween has an inherent reversibility, since, as the particles are randomly distributed in the enclosure, the same irregular pattern of flat surfaces and edged protrusions is also formed on the outer layer side of the enclosure. The padded sleeve may thus be turned inside out and still remains functional for the user. Hence, the idea of the especially advantageous embodiment described above is to add layer of flat and/or structured foam to the padded sleeve, upon which, on the inner layer side, the free polyhedral particles are added. This results, in the case of a flat foam layer, in one side of the sleeve having a flat topography, and the other having the non-flat randomized topography already discussed above. Depending on the patient's changing condition, in particular the stage of therapy, one side may be more desirable. For example, for mild lymphedema, flat non-aggressive foam surfaces are often preferred. For severe lymphedema variable, more aggressive contact surfaces are preferred to help break up fibrotic tissue. As the patient's condition improves, the reversible padded sleeve allows the therapy to adapt accordingly.

While it is, on the one hand, possible to secure the side edges of a panel comprising the inner layer, the outer layer and the enclosure with the particles together, for example by sewing, to form the padded sleeve, in particular in its tubular form, embodiments of the current invention may also provide that the padded sleeve comprises a closure system, in particular at least one zipper and/or at least one hook-and-loop fastening system. In this manner, the padded sleeve may be more easily to don, at least in some cases, by wrapping around the body part and then closing it using the closure system. However, having the padded sleeve already closed and elastic to draw over the body part is preferred, since, in particular due to larger swellings, closing the padded sleeve on the body part may be difficult or cumbersome.

It should be noted that, in principle, the padded sleeve may also be provided with tensioning straps to adjust compression, as known from some compression devices in the state of the art, which is, however, less preferred.

The invention further concerns a method for manufacturing a compression garment, in particular a compression garment according to the invention, to apply compression to a body part of a patient, wherein, to produce a padded sleeve, an inner and an outer layer are sewn together along their
edges leaving an opening to the provided enclosure
between the layers,
the enclosure is filled with a multiplicity of particles, in
particular plastic foam particles, for being pressed
against the body part, wherein the particles have an at
least essentially polyhedral shape such that an irregular
pattern of flat surfaces and edged protrusions is formed
at least on the inner layer side of the enclosure, and
the opening is closed by sewing.

All features and remarks regarding the compression gar-
ment according to the invention analogously apply to the
method according to the invention, such that the same
advantages can be achieved.

According to the method, and inner and outer layer,
preferably made from a fabric engineered to draw heat and
moisture away instantly and continuously from the body
part, are provided. These layers are sewn together to form a
"pillow case" type panel with an opening to add the particles
to the enclosure. The particles are preferably uniform poly-
hedral particles and may preferably consist of high-density
foam, which is water jet or die cut from sheet foam into
cubes with a consistent dimension of, preferably, 0.75 to
1.75 cm edge length.

When randomly placed into the panel enclosure, the
polyhedral, in particular cubed, particle geometry provides
for randomized flat surface and contoured surface protru-
sions of the inner layer to distribute compression to the body
part. After the enclosure is filled with the foam particles, the
padded sleeve is sewn shut. Before or after this process, the
compression garment may be preferably quilted along at
least one quilt seam.

That is, seams are quilted through the composite (i.e. the
outer layer, the, preferably foam, particles, and the inner
layer), thereby compressing portions of the particles, such
that channels are created in the panel, as already described
above. The panel may then be releasably or non-releasably
secured together on opposing side edges, forming the, in
particular tubular, padded sleeve shape.

Other objects and features of the present invention will
become apparent from the following detailed description
considered in conjunction with the accompanying drawings.
The drawings, however, are only principle sketches
designed solely for the purpose of illustration and do not
limit the invention. The drawings show:

DETAILED DESCRIPTION OF THE DRAWINGS

In the following, multiple embodiments of padded sleeves
and compression garments are exemplarily described. Each
compression garment according to the invention comprises
at least one padded sleeve, in some embodiments discussed
here two padded sleeves. However, in principle, the number
of padded sleeves is not so limited. The same holds true for
the optional oversleeves and undersleeves, which may be
provided as one or more exchangeable and/or combinable
sleeves. In particular, a compression garment system that is
configurable to provide different compressions and/or, in
particular graduated, compression profiles may be created.

Certain features only discussed with respect to one
embodiment may, of course, be transferred to other embodi-
ments described here, where applicable, in particular regard-
ing materials, shapes of components, fastening systems,
and/or indicia/marking systems.

Figure 1:
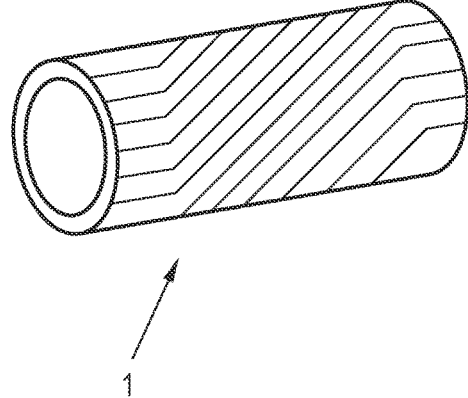
FIG. 1 a principle drawing of a padded sleeve of an
embodiment of a compression garment according to the
invention,
FIG. 2A a foam particle,
FIG. 2B a layer structure during manufacture of the
padded sleeve,
FIG. 2C the layer structure of FIG. 2B after quilting,
FIG. 3 a cross section of the padded sleeve,
FIG. 4A a layer structure for a second embodiment of a
padded sleeve,
FIG. 4B the layer structure of FIG. 4A after quilting,
FIG. 5 a layer structure for a third embodiment of a
padded sleeve,
FIG. 6 a schematic view of a padded sleeve having
different structure areas,
FIG. 7A-D examples of channel patterns for a padded
sleeve for the arm of a patient,
FIG. 8 a first embodiment of a compression garment with
an oversleeve, FIG. 9A-B alternative embodiments of the oversleeve of
FIG. 8,
FIG. 10 a second embodiment of a compression garment
with an oversleeve,
FIG. 11 a combined view of the padded sleeve and the
oversleeve of the second embodiment of FIG. 10,
FIG. 12 a cross-sectional view of the combined sleeves of
FIG. 11,
FIG. 13 a third embodiment of a compression garment
with oversleeves,
FIG. 14 a combined view of the padded sleeves and the
oversleeves of the third embodiment of FIG. 13,
FIG. 15 a fourth embodiment of a compression garment
with an undersleeve,
FIG. 16 a combined view of the padded sleeve and the
undersleeve of the fourth embodiment of FIG. 10, and
FIG. 17 a fifth embodiment of a compression garment for
the leg of a patient.

FIG. 1 shows a principle drawing of a padded sleeve 1 of
a compression garment according to the invention. The
padded sleeve 1 is, in this case, tubular and hollow to receive
a body part, in particular a limb, therethrough. To this end,
the padded sleeve 1 may be elastic and/or comprise a closure
system (not shown). In some, less preferred embodiments,
the padded sleeve 1 may also comprise straps for adjusting
compression. The straps and the closure system may be
combined.

Figure 2A:
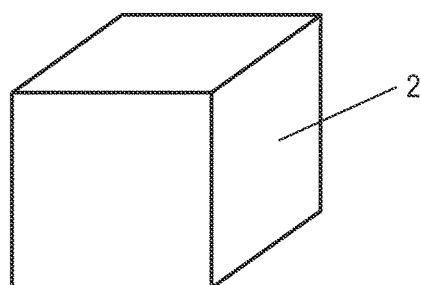
Figure 2B:
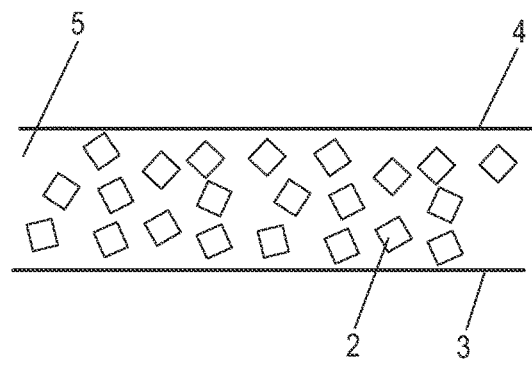
Figure 2C:
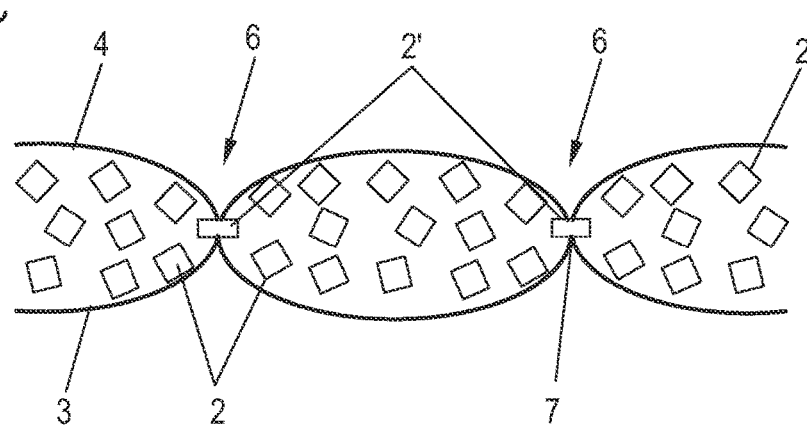

Regarding FIGS. 2A to 2C, the manufacturing of the
padded sleeve 1 is explained. For the padding of the padded
sleeve 1, foam particles 2 as indicated in FIG. 2A are used.
The foam particle 2 in this case has the shape of a cube, but
may, in other embodiments, also comprise other polyhedral
shapes, for example tetrahedrons or cuboctahedrons. For
example, the particles may be made from polyurethane foam
and preferably have a density between 2 and 3.5 pounds per
cubic foot, in this case between 2.5 and 2.9 pounds per cubic
foot. The impression load deflection (ILD) firmness may be
50 to 80, preferably 60 to 70. To form the cubes, the particles
2 are water jet cut or die cut from a foam sheet.

In the following, when particles 2 are shown in a formed
enclosure 5 in the padded sleeve 1, for simplicity, they may
be shown separated and spaced. However, it is understood
that, in reality, the particles 2 are touching each other,
contacting, in particular partly along edges or at corners,
and, due to the random insertion, create smaller, randomly
distributed spaces between them.

To manufacture the padded sleeve 1, an inner layer 3 and
an outer layer 4 are sewed together to form a panel which may be compared to a pillow case, wherein the panel has an opening to add the foam particles 2 into the formed enclosure 5, as indicated in FIG. 2B. The inner and outer layers 3, 4 are, in this case, identical, and are fabric layers. A moisture-wicking and temperature regulating fabric that draws heat and moisture away instantly and continuously from the body part, like materials known by the trademark "brrr°", is used.

The particles 2 have a dimension along their edges of 0.75 to 1.75 cm, in the current embodiment ½ inch. When placed inside the enclosure 5, the cubed geometry of the particles provides, as indicated in the figures, for an irregular pattern of flat surfaces and edged protrusions on at least the inner layer side of the enclosure 5, since the particles 2 are placed randomly in the enclosure 5. This transfers to an irregular combination of flat surfaces and contoured surface protrusions in the contact surface topography of the inner layer 3 when pressed against the body part. The relatively large size and geometry of the particles 2 also results in an increased air space between the particles 2, forming air passages to promote air, heat and moisture transfer to the outside of the padded sleeve 1.

The panel, after being filled with the particles 2 and hence showing the layer structure of FIG. 2B, is then closed by sewing. Thereafter, structuring seams 6 are quilted through the layer structure of FIG. 2B along defined paths thus creating a pattern of channels 7, as further discussed below. The stitches of the structuring seams 6, in this case kilt seams, not only extend through the inner and outer layers 3, 4, but also through the particles 2, such that some foam particles 2' are secured and compressed, padding the seam channel 7 areas. In consequence, as seen in FIG. 2C, the thickness varies along the panel, wherein thinner portions are found along the structuring seams 6.

The so-prepared panel may then be secured together at opposing ends, as already discussed with respect to FIG. 1, permanently or using a closure system. For example, opposing side edges may be sewed together.

The padded sleeve 1 may be configured for multiple body parts, but is preferably used for the upper extremities of a patient, that is, the arms. Here, the padded sleeve 1 may be configured to cover the hand, arm, and/or the shoulder, the latter using an oblique proximal rise. The padded sleeve 1 can be further configured to include a thumb post/thumb hole, quilted finger channel seems, or partial hand/arm coverage. Similar approaches can be applied to the lower extremities and other body parts, for example the head, the neck or the trunk.

Figure 3:
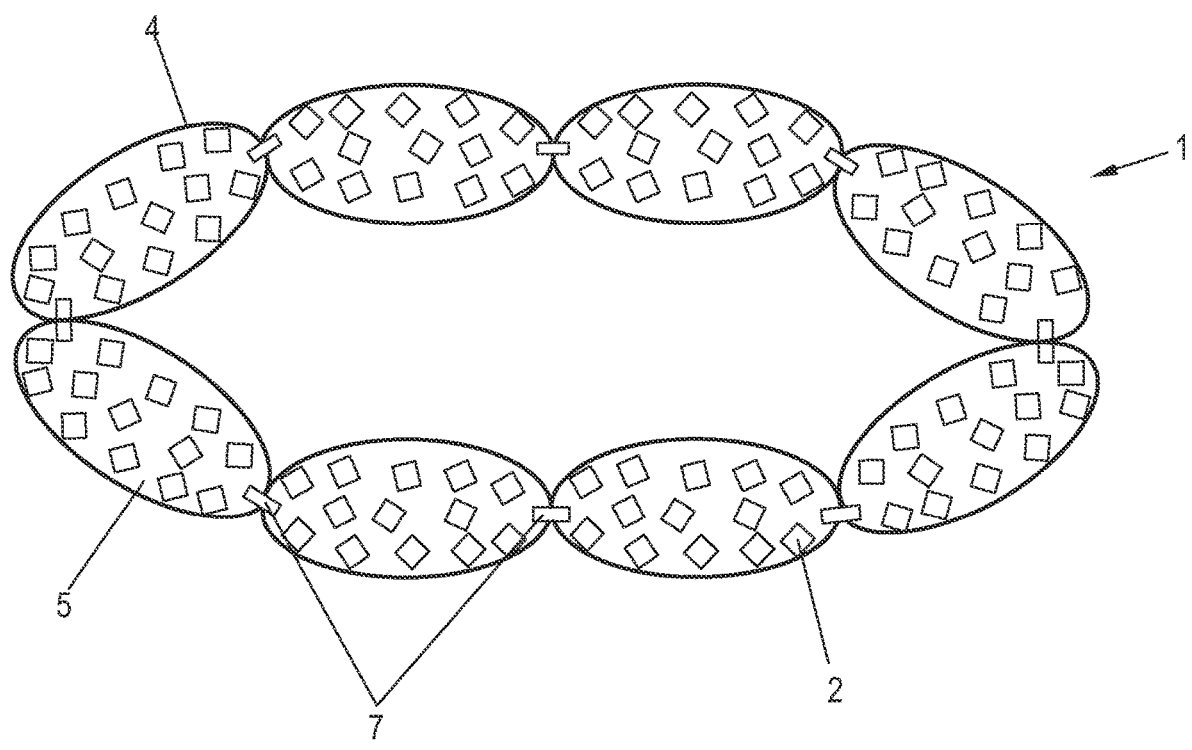

FIG. 3 shows a cross sectional view of the headed sleeve 1. As can be seen, by using the quilted seams 6, multiple channels 7 and sub-enclosures filled with foam particles 2 are formed. In this case, as can be seen, only cubically formed particles 2 are found in the enclosure 5, such that the irregular pattern can be found on the inner layer side as well as on the outer layer side, making the padded sleeve 1 in principle reversable. Upon reversing the padded sleeve 1, the former inner layer 3 becomes the outer layer and the former outer layer 4 becomes the inner layer.

Figure 4A:
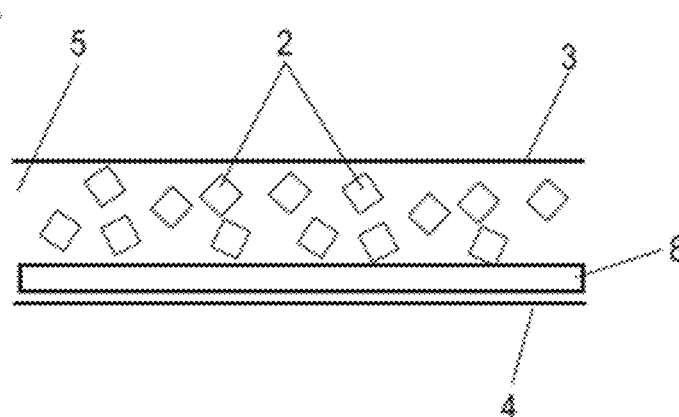
Figure 4B:
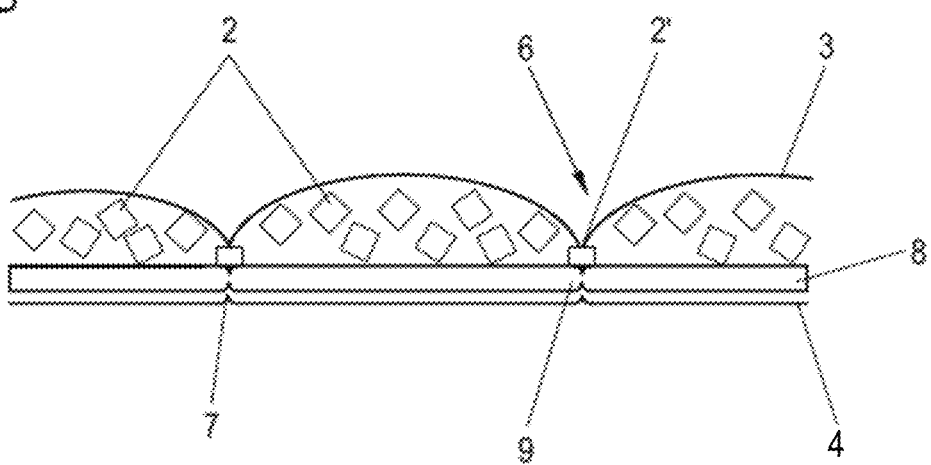

In this context, FIGS. 4A and 4B show an alternative embodiment of the layer structure that can be employed in the padded sleeve 1. In this case, on the outer layer side of the enclosure 5, a flat foam layer 8 is provided before the particles 2 are randomly inserted to the inner layer side of the enclosure 5. When the structuring seams 6 are quilted through the whole layer structure, also the flat foam layer 8 is fixed and compressed at positions 9. In this case, an irregular contact surface topography of the inner layer 3 towards the patient is provided by the particles 2, whereas a flat, second contact surface topography, also with channels 7, is provided for the outer layer 4. By respectively reversing the padded sleeve 1, both contact surface topographies may be applied to the patient. It is noted that, as an alternative to the flat foam layer 8, also a regularly structured foam layer may be employed.

Figure 5:
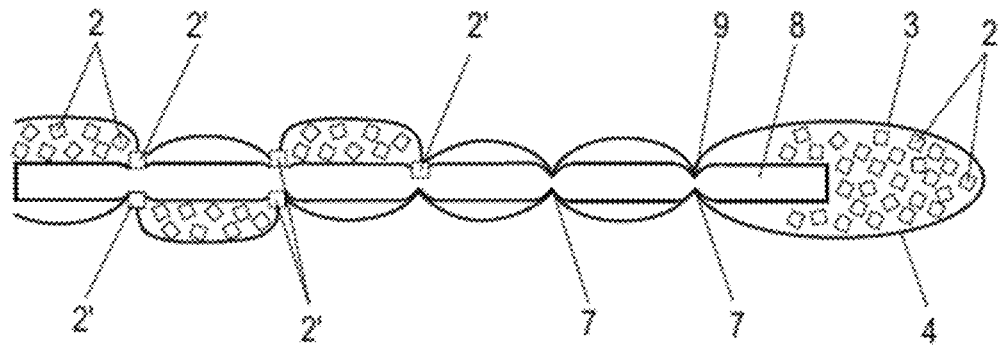

The contact surface topography may, according to the invention, also vary along the proximal-distal-direction, as indicated in FIG. 5. FIG. 5 shows a layer structure of the padded sleeve 1 explaining the possibilities for providing different structure areas along the padded sleeve 1. Free particles 2 and sheet foam layers 8 can be placed in parallel layers or alternated in series, or any combination of both. This allows for different topographies and compression effects at different areas of the body part.

Figure 6:
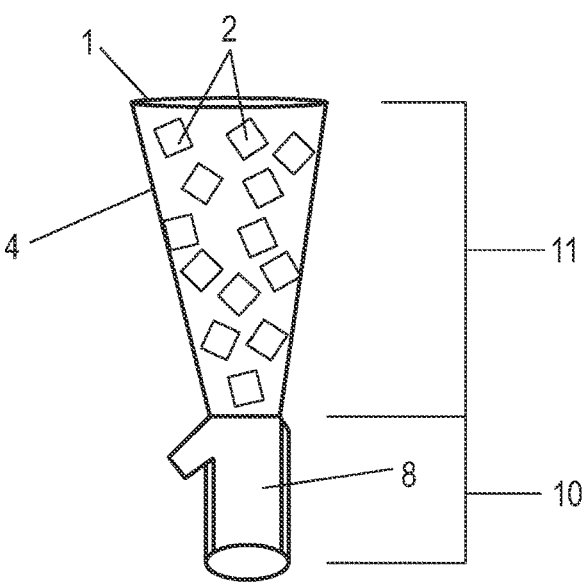

For example, a padded sleeve 1 to be applied to the arm and hand of a patient is shown as a principle drawing in FIG. 6. Two structure areas 10, 11 are shown, wherein, in the structure area 10, a flat foam layer 8 is used, while in the structure area 11, the particles 2 in the enclosure 5 are employed. The structure area 10 is provided for the hand area, while the structure area 11 is provided for the arm. It is, however, noted that, alternatively, two padded sleeves 1 may be provided.

Figure 7A:
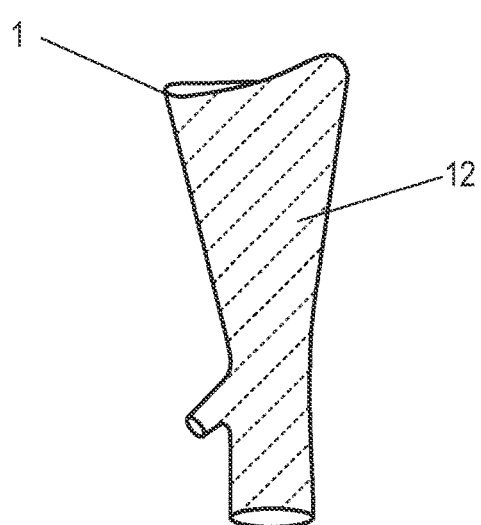
Figure 7B:
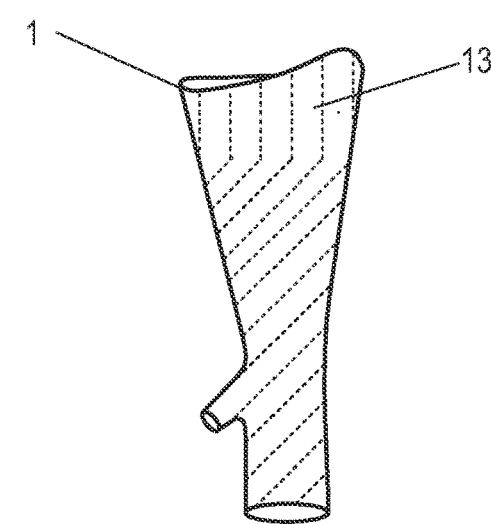
Figure 7C:
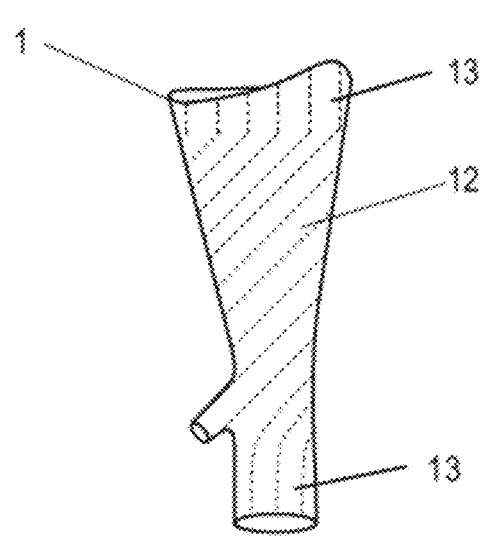
Figure 7D:
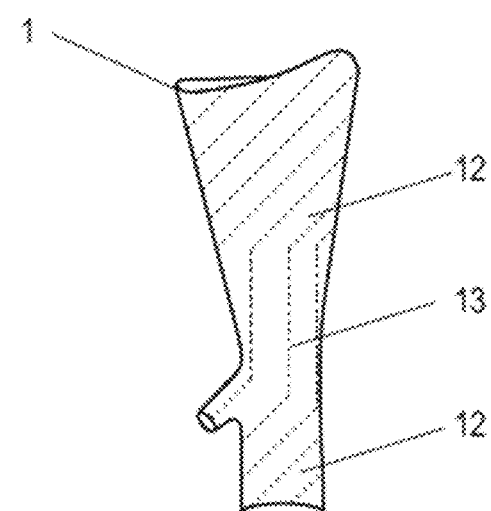

As already discussed, by using the structuring seams 6, certain patterns of channels can be provided. Exemplary embodiments are shown in FIGS. 7A to 7D for a padded sleeve 1 to be worn on the arm and hand of a patient. FIG. 7A shows an embodiment only comprising a chevron pattern 12 of channels extending over the whole padded sleeve 1. In FIG. 7B, the chevron pattern 12 transitions into a straight pattern 13 at the proximal end of the padded sleeve 1. The preferred embodiment is shown in FIG. 7C, where a straight pattern 13 at the distal end in the hand area transitions to a chevron pattern 12 in the central area, which again transitions into a straight pattern 13 at the proximal end. Finally, a pattern of channels 7, wherein chevron patterns 12 at the ends transition into a straight pattern 13 the central region is shown.

Figure 8:
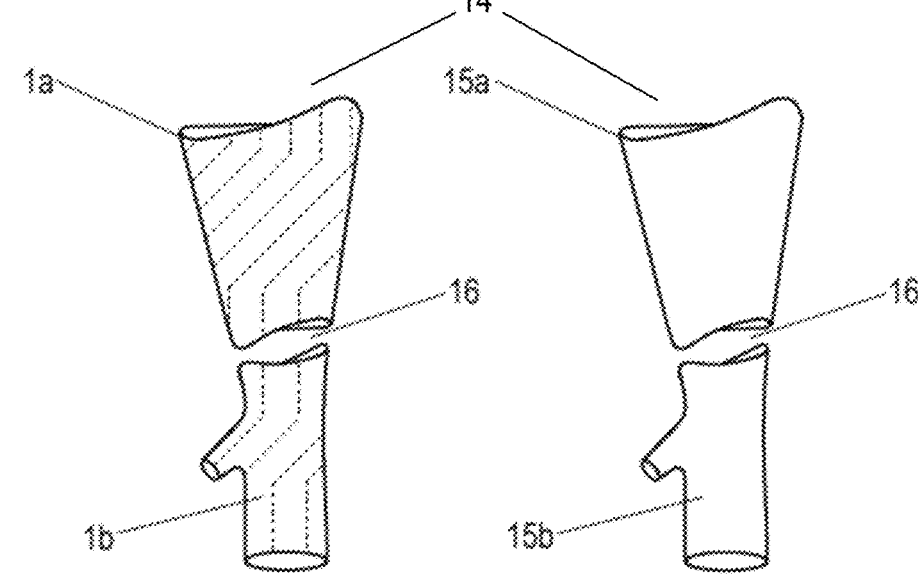

In the following, concrete embodiments of compression garments using such padded sleeves 1 are shown. In FIG. 8, a compression garment 4 for the arm and hand of a patient having two padded sleeves 1a, 1b, one for the arm, one for the hand, and two oversleeves 15a, 15b for the respective padded sleeves 1a, 1b is shown. At the paired sleeve end junction 16, as can be seen, the shared edges of the padded sleeves 1a, 1b that abut each other when donned follow the chevron pattern angle. The paired sleeve end junction 16 serves as a low-pressure channel similar to the channels 7 provided by the structuring seems 6 kilted through the padded sleeves 1a, 1b. The angular extension areas of the padded sleeves 1a, 1b also provide a region of little to no compression. The oversleeves 15a, 15b are configured to be worn over the padded sleeves 1a, 1b to apply additive compression to both the padded sleeves 1a, 1b as well as the angular extension areas.

Figure 9A:
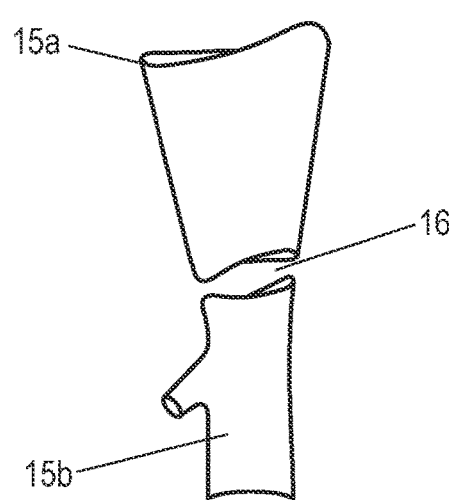
Figure 9B:
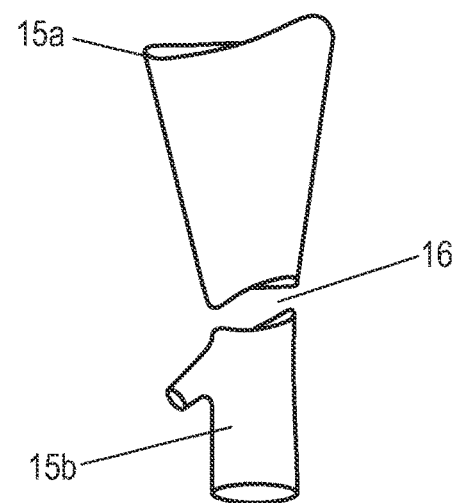

As shown by the alternative oversleeves 15a, 15b of FIGS. 9A and 9B, the paired sleeve end junctions 16 of the oversleeves 15a, 15b and the padded sleeves 1a, 1b are not required to match, which may lead to increased stability. It should further be noted already at this point that multiple oversleeves 15a and/or 15b may be provided each having different compression characteristics to be able to apply different effective compression profiles to the body part by choosing the respective combination of padded sleeve 1a, 1b and oversleeve 15a, 15b, as further discussed below for further embodiments.

Figure 10:
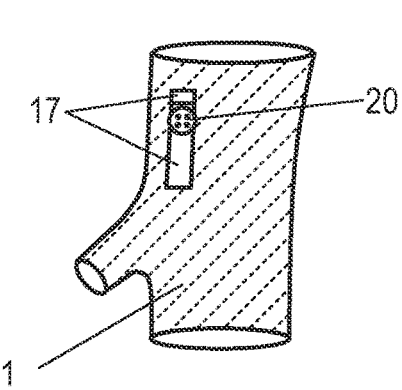
Figure 11:
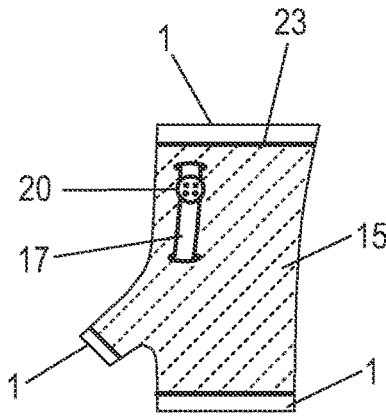
Figure 12:
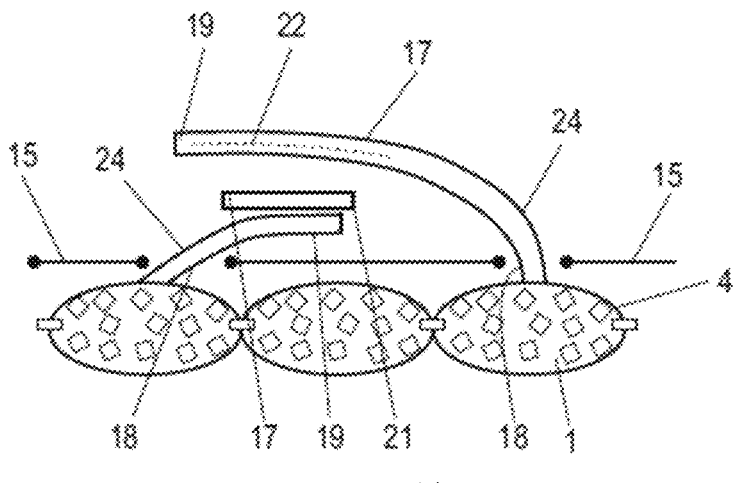

FIGS. 10 to 12 show a second embodiment of a compression garment 14, again for use at the arm and hand. As can be seen, in this embodiment, the padded sleeve 1 comprises a donning band 17 secured to its outer layer 4. The donning band 17 can be used to aid in donning or undonning the compression garment 14, since it forms a handle strap allowing to don at least the padded sleeve 1 over the body part, in this case arm and hand. It should be noted at this point that also an undersleeve (not shown in FIGS. 10 to 12) having an outer low friction surface may be provided as part of the compression garment 14 upon which the padded sleeve 1 may slide to provide easier donning. The two-part donning band 17 comprises two fixed ends 18 sewn to the outer layer 4 and to free ends 19 detachably fastenable to each other by a fastener 20, in this case a button-and-loop-fastener having a button 21 passing through a perforation 22 in the other free end to attach the free ends 19 together.

The compression garment 14 further comprises an oversleeve 15, wherein the oversleeve 15, as shown in the combined view of FIG. 11, is shorter than the padded sleeve 1 such that its finished edges 23 do not touch the skin of the patient, possibly causing irritations.

The oversleeve 15 further comprises two perforations 24, through which the free ends 19 of the donning band 17 may be guided and then again fastened together using the fastener 20. In FIG. 12, the parts of the donning band 17 passing through the perforations 24 are clearly shown.

In other words, the parts of the donning band 17 are secured to the padded sleeve 1 and connected using a button 21. When released from the button 21, the donning band 17 can be threaded through openings 24 of the oversleeve 15, allowing the donning band 17 to be used to assist in donning both the padded sleeve 1 and the oversleeve 15 simultaneously, where otherwise the donning band 17 would be covered by the oversleeve 15. In an additional functionality, the donning band 17 secures the oversleeve 15 in place and the button 21 can be further utilized as an anker for additional oversleeves 15.

Figure 13:
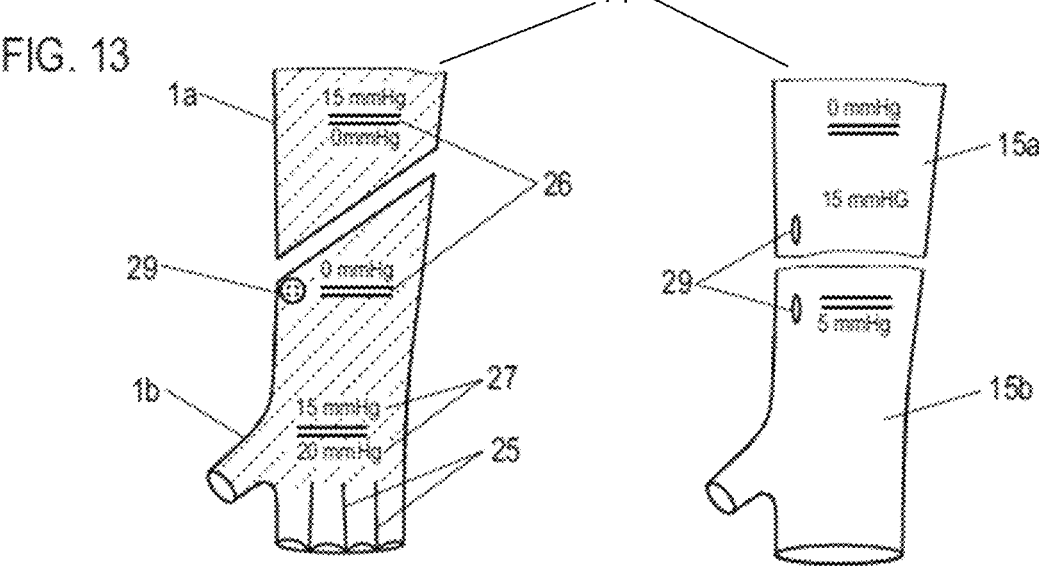
Figure 14:
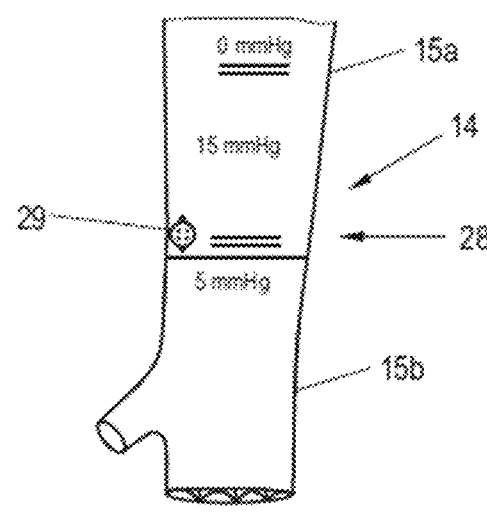

FIGS. 13 and 14 show a third embodiment of a compression garment 14 for the arm and hand of a patient, in this case again comprising two padded sleeves 1a, 1b, one for the arm and one for the hand, and two oversleeves 15a, 15b, again one for the arm and one for the hand. In the padded sleeve 1b, finger channels for receiving the fingers have been provided by quilting opposing parts of the whole padded sleeve 1b together using finger channel seams 25. Furthermore, each sleeve 1a, 1b, 15a, 15b comprises alignment indicia 26 of a marking system as well as compression indicia 27 of a labelling system. The alignment indicia 26 serve to indicate how interfacing sleeves 1a, 1b, 15a, 15b are to be correctly positioned. In this case, the oversleeves 15a, 15b are supposed to partly overlap in a compression zone 28, which is also exploited by providing fastening means 29 for both the padded sleeve 1b as well as both oversleeves 15a, 15b to detachably fasten the oversleeves 15a, 15b to the padded sleeve 1b in the correct position. To this end, the fastening means 29 comprise through-holes for perforations in the oversleeves 15a, 15b, and a button to pass through both through-holes, as illustrated in FIG. 14. Of course, additionally, a donning band 17 as described above may be employed, for example at the proximal end of the padded sleeve 1a.

Each of the sleeves 1a, 1b, 15a, 15b has certain compression characteristics, in particular compression zones in which a certain compression onto the body part is exerted, wherein these compression zones and their compression are indicated by the compression indicia 27. The compression zones, in this example, are separated by the alignment indicia 26. When the compression garment 14 of FIG. 13 is worn as shown in FIG. 14, four compression zones result. In the finger area, the compression of 20 mmHg of the padded sleeve 1b and 5 mmHg of oversleeve 15b add up to a total compression of 25 mmHg. In a hand compression zone proximally adjacent, 15 mmHg from the padded sleeve 1b and 5 mmHg from the oversleeve 15b add up to yield a compression of 20 mm. In a lower arm compression zone, the respective 0 mmHg compression of the sleeves 1a and 1b add up with the compression of 15 mmHg of the oversleeve 15a to yield 15 mmHg in total. Finally, in an upper arm compression zone, a 15 mmHg of the padded sleeve 1a add up with 0 mmHg of the oversleeve 15a to provide, again, a total of 15 mmHg. Hence, a graduated compression profile (25 mmHg, 20 mmHg, 15 mmHg, and 15 mmHg) is provided in a distal-proximal-direction, facilitating flow of edema fluid.

It is noted that multiple oversleeves 15a, 15b each having different compression characteristics may be provided to be able to configure the compression garment 14 to an effective compression profile as desired. For example, the basic compression profiles provided by the padded sleeves 1a, 1b and additional compression profiles provided by oversleeves 15a, 15b may be combined to an effective compression profile according to a compression class according to a standard, like RAL-GC 387/2. Here, preferably, oversleeves 15a, 15b are provided such that at least compression class I and compression class II (mild and moderate compression, respectively) may be adjusted on the patient. In this case, an embodiment, the compression indicia 27 may additionally or alternatively indicate compression classes.

It is noted that such combinations to implement desired effective compression profiles may alternatively or additionally also be achieved using undersleeves.

Figure 15:
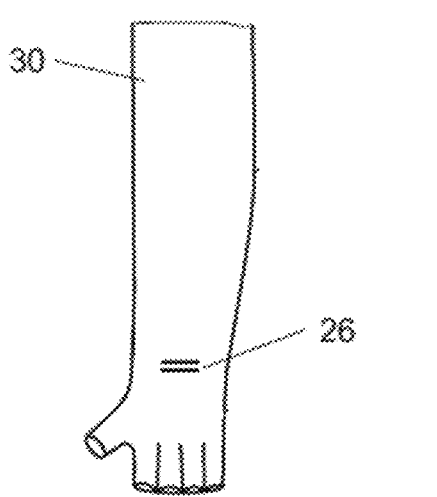
Figure 15:
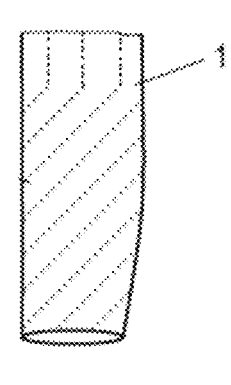
Figure 16:
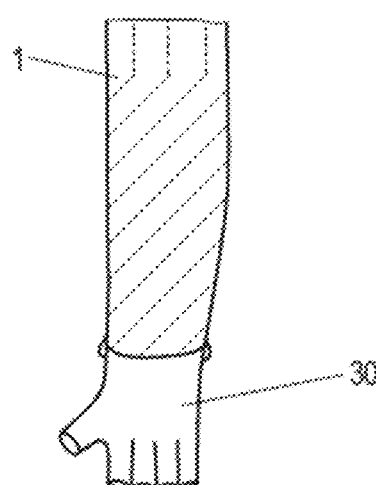

In a fourth embodiment according to FIGS. 15 and 16, the compression garment 14 comprises a padded sleeve for the arm and an undersleeve 30 covering the arm and the hand. Alignment indicia 26a in positioning the padded sleeve 1 over the undersleeve 30, wherein, furthermore, compression indicia 27 indicate compression, in this case ranges. The undersleeve 30 has a low friction outer surface to facilitate donning the padded sleeve 1.

In this embodiment, the undersleeve 30 exerts a compression of 15 to 20 mmHg in the hand area and 0 to 10 mmHg in the arm area. The padded sleeve 1 exerts a compression of 0 to 10 mmHg in the arm area, such that, in the arm area, the basic compression profile of the padded sleeve 1 adds up with the additional compression profile of the undersleeve 30, wherein, in the hand area, only the additional compression profile of the undersleeve 30 defines the effective compression profile.

Figure 17:
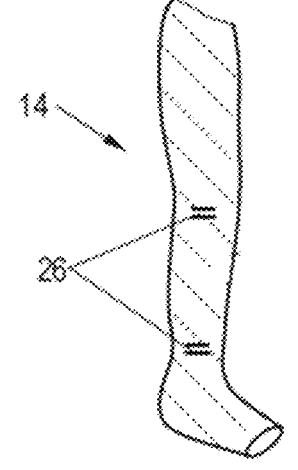
Figure 17:
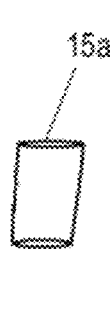
Figure 17:
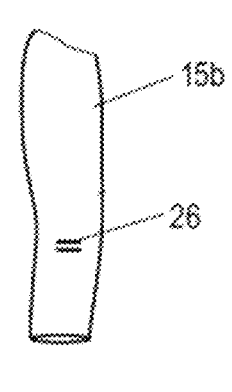
Figure 17:
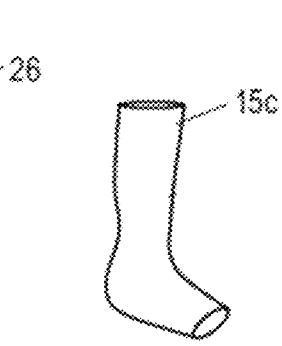

FIG. 17 finally illustrates a compression garment applicable to the lower extremities, in this case covering the leg and partially the foot. A padded sleeve 1 is provided for both the foot and the leg, while exemplarily three oversleeves 15a, 15b and 15c for different portions of the body part, in this case the lower leg, the lower leg and foot, and the upper and lower leg, are provided, wherein, again, alignment indicia 26 of a marking system for correct positioning of the oversleeve 15a, 15b and 15c are provided. Additionally, compression indicia 27 of a labeling system are printed on the sleeves 1, 15a, 15b, 15c to indicate compression levels provided, such that, by combining the padded sleeve 1 with respective combinations of oversleeves 15a, 15b and 15c, desired effective compression profiles can be adjusted.

It is noted that also for the embodiments of FIGS. 15 to 17, of course, fastening means 29 may be provided to detachably secure the oversleeves 15, 15a, 15b, 15c on the padded sleeve 1 and/or the undersleeve 30 and/or the padded sleeve 1 on the undersleeve 30.

We claim:

1. A compression garment for providing compression to a body part of a patient, comprising a padded sleeve configured to extend around the body part and having:

an elastic inner layer and an elastic outer layer secured together to define at least one enclosure between them, and multiple particles, received randomly in the enclosure, contacting each other and forming free spaces between the multiple particles, wherein the padded sleeve is configured to apply compression to and press the multiple particles against the body part, wherein the multiple particles have a polyhedral shape such that an irregular pattern of flat surfaces and edged protrusions is formed at least on the inner layer side of the at least one enclosure, wherein edges of the multiple particles have a length of at least 0.75 cm, wherein the padded sleeve comprises at least one structuring seam structuring the padded sleeve, and wherein the at least one structuring seam is at least one quilt seam, and wherein at least one stitch of the at least one quilt seam extends through at least one of the multiple particles to compress the at least one of the multiple particles such that the padded sleeve is of less thickness at the at least one quilt seam.

2. The compression garment of claim 1, wherein the multiple particles have the same dimensions and/or wherein the multiple particles are of the same shape and/or are tetrahedrons or cubes and/or are made of high-density foam.

3. The compression garment of claim 1, wherein the multiple particles arranged in the at least one enclosure form air passages from the inner layer to the outer layer and/or the inner layer and the outer layer are made of a fabric.

4. The compression garment of claim 1, wherein the at least one structuring seam comprises multiple structuring seams and the multiple structuring seams define a pattern of channels extending over the area of the padded sleeve.

5. The compression garment of claim 4, wherein the pattern of channels is or comprises a chevron pattern and/or comprises multiple sub-patterns whose channels at least partly connect to each other, wherein, in a proximal-distal direction, a central chevron pattern transitions to a straight and/or a fanned pattern at a distal and/or a proximal end of the padded sleeve.

6. The compression garment of claim 1, wherein the padded sleeve is elastic and/or configured to apply compression according to a predetermined basic compression profile to the body part.

7. The compression garment of claim 1, further comprising at least one oversleeve, which is adapted to be worn over the padded sleeve, and/or at least one undersleeve, which is adapted to be worn under the padded sleeve, wherein the at least one oversleeve and/or the at least one undersleeve comprise at least one fabric layer and are configured to apply compression according to a predetermined additional compression profile to the body part.

8. The compression garment of claim 7, wherein multiple oversleeves and/or undersleeves for selectively applying to the patient are provided and/or the compression applied by at least one of the at least one oversleeve and/or at least one of the at least one undersleeve is in the range of 0 to 10 mmHg and/or of 5 to 15 mmHg.

9. The compression garment of claim 7, wherein a basic compression profile and the additional compression profile are chosen such that they combine to an effective compression profile according to at least one compression class according to at least one guideline or standard.

10. The compression garment of claim 7, wherein at least one of the at least one oversleeve is shorter in a proximal-distal-direction than the padded sleeve.

11. The compression garment of claim 7, wherein multiple oversleeves and/or undersleeves of different dimensions or shapes for selectively applying to the patient are provided for covering different portions of the body part and/or the padded sleeve.

12. The compression garment of claim 7, wherein at least one of the at least one undersleeve, the at least one oversleeve, and the padded sleeve comprises indicia for positioning the padded sleeve on the at least one of the at least one oversleeve and the at least one undersleeve.

13. The compression garment of claim 7, wherein the at least one oversleeve and the padded sleeve comprise corresponding fastening means for detachably fastening the at least one oversleeve to the padded sleeve in at least one position, wherein the fastening means on the padded sleeve comprises at least one donning band, each of the at least one donning bands having two fixed ends secured to the outer layer and two free ends detachably fastened to each other by a fastener, and wherein the fastening means of the at least one oversleeve comprise two perforations for the at least one donning band.

14. The compression garment of claim 1, wherein the padded sleeve comprises at least one donning band on the outer layer.

15. The compression garment of claim 1, wherein the padded sleeve comprises multiple different structure areas along a proximal-distal direction, wherein at least one structure area comprises the multiple particles in the at least one enclosure resulting in an irregular contact surface topography of the inner layer towards the patient, while at least one other structure area comprises a different, second contact surface topography, wherein a flat or regularly structured foam layer is arranged between the inner and the outer layers to provide the second contact surface topography.

16. The compression garment of claim 1, wherein the padded sleeve further comprises at least one foam layer between the multiple particles and the outer layer in the at least one enclosure, the at least one foam layer having an outer layer side topography differing from the inner layer side topography provided by the multiple particles such that the padded sleeve can be reversed to apply the outer layer side topography to the body part.

17. A method for manufacturing a compression garment of claim 1, comprising:

sewing an inner and an outer layer together along their edges and leaving an opening to provid an enclosure between the inner layer and the outer layer, filling the enclosure with multiple particles, the multiple particles are to be pressed against the body part, wherein the particles have an essentially polyhedral shape such that an irregular pattern of flat surfaces and edged protrusions is formed at least on the inner layer side of the enclosure, wherein edges of the multiple particles have a length of at least 0.75 cm, sewing at least one structuring seam on the padded sleeve, wherein the at least one structuring seam is at least one quilt seam, and wherein at least one stitch of the at least one quilt seam extends through at least one of the multiple particles to compress the at least one of the multiple particles such that the padded sleeve is of less thickness at the at least one quilt seam, and sewing to close the opening.

18. The method of claim 17, further comprising quilting the compression garment along at least one quilt seam before or after the opening has been closed by sewing.

\* \* \* \* \*